(12) United States Patent
Vander Hooven

(10) Patent No.: US 6,479,062 B2
(45) Date of Patent: Nov. 12, 2002

(54) PESTICIDE BAIT CARRIER

(76) Inventor: David I. B. Vander Hooven, 1124 Fort St., Maumee, OH (US) 43537

( * ) Notice: Subject to any disclaimer, the term of this patent is extended or adjusted under 35 U.S.C. 154(b) by 0 days.

(21) Appl. No.: 09/960,411

(22) Filed: Sep. 21, 2001

(65) Prior Publication Data

US 2002/0037307 A1 Mar. 28, 2002

Related U.S. Application Data

(63) Continuation-in-part of application No. 09/491,062, filed on Jan. 25, 2000.
(60) Provisional application No. 60/135,892, filed on May 26, 1999, and provisional application No. 60/117,739, filed on Jan. 29, 1999.

(51) Int. Cl.[7] .............................................. A01N 25/12
(52) U.S. Cl. ....................... 424/410; 424/406; 424/417; 424/442; 424/DIG. 10; 424/DIG. 11; 424/408
(58) Field of Search ................................. 424/442, 405, 424/408, 409, 417, 84, DIG. 10, DIG. 11, 410, 406

(56) References Cited

U.S. PATENT DOCUMENTS

| | | |
|---|---|---|
| 4,049,460 A | 9/1977 | Broudbent ................ 106/15 R |
| 4,205,066 A | 5/1980 | Hennart et al. ............... 424/84 |
| 4,320,130 A | 3/1982 | Balsley et al. |
| 4,363,798 A | 12/1982 | D'Orazio |
| 4,560,527 A | 12/1985 | Harke et al. |
| 4,563,344 A | 1/1986 | Kotz et al. |
| 4,621,011 A | 11/1986 | Fleischer et al. |
| 4,657,912 A | 4/1987 | Suzuki et al. ................ 514/275 |
| 4,874,611 A | 10/1989 | Wilson et al. |
| 4,944,950 A | 7/1990 | Sakharova |
| 4,985,413 A | 1/1991 | Kohama et al. |
| 5,019,564 A | 5/1991 | Lowe et al. |
| 5,062,954 A | 11/1991 | Leedy et al. |
| 5,064,407 A | 11/1991 | Peiffer |
| 5,118,506 A | 6/1992 | Eichoefer |
| 5,186,935 A | 2/1993 | Tucker |
| 5,207,389 A * | 5/1993 | Hall et al. |
| 5,219,818 A | 6/1993 | Ivie |
| 5,229,348 A * | 7/1993 | Ivie |
| 5,270,044 A * | 12/1993 | Fulmer et al. |
| 5,547,955 A * | 8/1996 | Silerman et al. |
| 5,609,880 A * | 3/1997 | Munson et al. |
| 5,635,174 A * | 6/1997 | Warren et al. |
| 5,679,365 A | 10/1997 | Henderson et al. |
| 5,707,640 A * | 1/1998 | Wada et al. |
| 5,820,855 A * | 10/1998 | Barcay et al. |
| 5,843,203 A * | 12/1998 | Lindsay et al. |
| 5,850,707 A * | 12/1998 | Fell et al. |
| 5,939,061 A * | 8/1999 | Vail et al. |

OTHER PUBLICATIONS

Nutro—Max 1993.
Nutro—Natural Choice 1999.

* cited by examiner

Primary Examiner—Neil S. Levy
(74) Attorney, Agent, or Firm—Emch, Schaffer, Schaub & Porcello Co., L.P.A.

(57) ABSTRACT

A bait carrier for pesticides comprising a waste product selected from the group consisting of bakery waste, confectionery waste, snack waste and cereal waste. The waste product has a particle size between 6 mesh and 100 mesh and a density between 6 pounds per cubic foot and 40 pounds per cubic foot. After production of the bait carrier, pesticides are added to the carrier by others. The bait carrier serves as an attractant bait for delivery of the pesticide to a pest.

16 Claims, No Drawings

PESTICIDE BAIT CARRIER

RELATED APPLICATIONS

The present application is related to U.S. Provisional Patent Application Ser. No. 60/117,739 filed Jan. 29, 1999; U.S. Provisional Patent Application Ser. No. 60/135,892 filed May 26, 1999; and is a continuation-in-part of U.S. patent application Ser. No. 09/491,062 filed Jan. 25, 2000.

BACKGROUND OF THE INVENTION

The present invention is a pesticide bait carrier, not a pesticide itself, for use in eradicating pests. The carrier is particularly effective for use as a bait and pesticide carrier in eradicating imported fire ants, wherein others add the pesticide.

While imported fire ants have been found in the United States for years, their spread continues north and west. They presently are located in eleven southeastern states, Puerto Rico, New Mexico and in some urban areas of California. Over three hundred million acres are infested.

The use of bait carriers to control imported fire ants, termites, slugs, snails, mole crickets, household ants and roaches is known in the art. The primary carrier presently used is a prejelled, defatted corn grit. This bait carrier must be treated with soybean oil which serves as a vehicle to carry the insecticide, while acting as an attractant to the ant. A disclosure of such a prior art bait is found in U.S. Pat. No. 4,320,130.

The present invention utilizes food waste products such as bakery waste, confectionery waste, snack waste, and cereal waste. These wastes, when not processed into livestock and poultry feed, are deposited into landfills. This practice is costly and creates additional environmental problems for already burdened landfills. These wastes, unlike some agricultural by-products, such as corncobs, cannot be simply returned to the earth and plowed under to create humus. They must be landfilled.

The present invention utilizes food waste products in pesticide bait carriers.

SUMMARY OF THE INVENTION

The present invention is a bait carrier for pesticides comprising a waste product selected from the group consisting of:
(a) bakery waste;
(b) confectionery waste;
(c) snack waste; and
(d) cereal waste.

The waste product has a particle size between 6 mesh screen and 100 mesh screen (U.S. Standard Sieve Series) and a density between 6 pounds per cubic foot and 40 pounds per cubic foot. The carrier, according to the present invention, serves as an attractive bait for delivery of pesticides to pests.

DESCRIPTION OF THE PREFERRED EMBODIMENTS

The invention includes the use of waste products such as bakery waste, confectionery waste, snack waste and cereal waste, either alone or in combination with one another, as a bait carrier for pesticide chemicals. Bakery waste is a mixture of bakery products such as bread, cookies, cakes, crackers, flours and doughs which have been mechanically separated from non-edible material, artificially dried and ground. Confectionery waste is a mixture of confectionery products such as candy bars, hard candy, jelly beans, chocolates, chocolate syrup and flavored syrups that have been separated from non-edible material, artificially dried and ground. Snack waste is a mixture of snack food products such as potato chips, pretzels, corn chips, popcorn, caramel corn and cheese curls that have been separated from non-edible material, artificially dried and ground. Cereal waste is a mixture of cereal products such as wheat flakes, corn flakes, puffed rice, shaped oats, shredded wheat, oatmeal and rolled oats separated from non-edible material, artificially dried and ground.

The waste product is crushed, ground and reduced in size to where the majority of the particles pass through a 6 mesh screen and passes over a 100 mesh screen (U.S. Standard Sieve Series). The over 6 mesh screen particles are returned to the initial grinding process until the desired particle size is obtained or may be reconstituted to pass through the 6 mesh screen and over the 100 mesh screen. The preferred particle size is between a 10 mesh (pass through) and a 40 mesh (pass over). The resulting preferred product which passes through a 10 mesh screen and over a 40 mesh screen (−10+40) is controlled to have a bulk density between 6 and 40 pounds per cubic foot, with a density between 30 and 40 pounds per cubic foot being preferred.

In some bait carriers, according to the present invention, fats and oils such as soy bean oil will be added to the processed waste product particles as a vehicle to carry the pesticide and to act as an added attractant to the pest. The particles have the ability to absorb up to 20% soy bean oil and still remain flowable for easy field applications using spreaders, hand application or aerial application. Preferably, not more than 5% soy bean oil is added to the processed waste particles, if needed. Other examples of fats and oils that can be used include vegetable oils, pine oils and animal fats.

Some formulators make it is necessary to dilute the pesticide in an inorganic solvent such as acetone, to facilitate its addition to the bait carrier. This invention permits the use of such solvents with no adverse effects to the subject pesticide carrier bait, once the solvent has been evaporated.

While the particles are usually composed of bakery, confectionery snack and cereal wastes as ingredients to the overall final product, original food ingredients may be used to simulate such wastes. The mixture of original food ingredients may be prepared and processed the same as described above with respect to use of the wastes.

The particles are preferably shaped to accommodate different types of spreaders, such as aerial spreaders and cyclone-type spreaders. The shapes include spheres, generally flat oval platelets and pellets.

The processed particles are often dyed to a predetermined color. This aids the identification of different end use products with no adverse effects.

The following Table A shows the preferred ranges of the ingredients found in a pesticide bait carrier according to the present invention.

TABLE A

| Ingredient | % of Total Pesticide Bait Carrier (by weight) |
|---|---|
| Water | 5% to 20% |
| Protein | 5% to 20% |
| Fiber | 2% to 5% |

TABLE A-continued

| Ingredient | % of Total Pesticide Bait Carrier (by weight) |
| --- | --- |
| Ash | 3% to 8% |
| Fat (oil) | 0.5% to 20% |
| Carbohydrates | 40% to 70% |

It has been found that the bait carrier particles, according to the present invention, can be coated with conventional preservatives to prolong their field life and as an aid in retarding the loss of oil when the bait carrier particles are spread on hot concrete or soil.

The present invention, as set forth in Table A, has shown itself to be a successful attractant to most pests, however, by adding aromas such as sugar, molasses and wood flour, some targeted pests can be attracted more than others. Table B, below, shows the percentages, by weight, of these additives, as read in conjunction with Table A.

TABLE B

| Additive | Effect | Percent Added (by weight) |
| --- | --- | --- |
| Sugar | Broadens olfactory range | 1% to 7% |
| Molasses (liquid) | Sweetens the taste of the bait | 3% to 12% |
| Wood Flour | Encourages ingestion by wood eating insects | 1% to 10% |

The present invention, as set forth in Table A, has shown itself to be resilient to rainfall and high humidity when used in open areas, however, the addition of water repellent binder can increase its resistance to high moisture conditions without harming its attractiveness. Table C, below, shows the percentage, by weight, of this additive, as read in conjunction with Table A.

TABLE C

| Additive | Effect | Percent Added (by weight) |
| --- | --- | --- |
| Organic Water Repellent Binder | Prolongs life of product in wet conditions | 4% to 15% |

The present invention, as set forth in Table A, has shown itself to be free flowing, however, the addition of an anti-caking agent to reduce the tendency of individual particles to adhere to one another is effective without harming its attractiveness. Table D, below, shows the percentage, by weight, of this additive, as read in conjunction with Table A.

TABLE D

| Additive | Effect | Percentage (by weight) |
| --- | --- | --- |
| Anticaking Agent | Enhances flow-ability | 4% to 10% |

The present invention, as set forth in Table A, usually has inherent preservatives to prevent mold from occurring at moistures not above 14%, however, an antioxidant can be added to prolong the shelflife of the present invention. Antioxidants protect against deterioration of the bait carrier caused by oxidation, such as fat rancidity and color changes, without harming the carrier's attractiveness to pests. Table E, below, shows the percentage, by weight, of this additive, as read in conjunction with Table A.

TABLE E

| Additive | Effect | Percentage (by weight) |
| --- | --- | --- |
| Antioxidant | Prolongs shelflife in moistures over 14% | Not to exceed 0.5% |

A preferred embodiment of the present invention is set forth in the example as follows:

EXAMPLE

| Ingredient | % of Total Pesticide Bait Carrier (by weight) |
| --- | --- |
| Water | 7.5% |
| Protein | 11.3% |
| Fiber | 2.0% |
| Ash | 3.5% |
| Fat (oil) | 11.2% |
| Carbohydrates | 64.5% |

The above embodiment had a size from about 10 mesh to about 40 mesh (−10+40), U.S. Standard Sieve Series, and a density of about 35 pounds per cubic foot.

Many revisions may be made to the pesticide bait carrier of the present invention without departing from the scope of the invention or from the following claims.

I claim:

1. A bait carrier for a pesticide including food waste comprising from about 40% to about 70%, by weight, carbohydrates; from about 5% to about 20%, by weight, protein; from about 10% to about 20%, by weight, fat; and from about 5% to about 20%, by weight, water, said bait carrier having a size from about 6 mesh to about 100 mesh, U.S. Standard Sieve Series, and a density from about 6 pounds per cubic foot to about 40 pounds per cubic foot.

2. The bait carrier of claim 1, wherein said food waste being selected from the group consisting of bakery food waste, confectionery food waste, snack food waste and cereal food waste.

3. The bait carrier of claim 1, wherein said fat being selected from the group consisting of soy bean oil, vegetable oil, pine oil and animal fat.

4. The bait carrier of claim 1, wherein said bait carrier further comprising from about 3% to about 8%, by weight, ash.

5. The bait carrier of claim 1, wherein said bait carrier further comprising from about 2% to about 5%, by weight, fiber.

6. The bait carrier of claim 1, wherein said bait carrier further comprising dye to provide coloration to said bait carrier.

7. The bait carrier of claim 1, wherein said bait carrier has a pellet shape.

8. The bait carrier of claim 1, wherein said bait carrier has a spherical shape.

9. The bait carrier of claim 1, wherein said bait carrier has a platelet shape.

10. The bait carrier of claim 1, wherein said bait carrier further comprises from about 1% to about 7%, by weight, sugar.

11. The bait carrier of claim 1, wherein said bait carrier further comprises from about 3% to about 12%, by weight, molasses.

12. The bait carrier of claim 1, wherein said bait carrier further comprises from about 1% to about 10%, by weight, wood flour.

13. The bait carrier of claim 1, wherein said bait carrier further comprises from about 4% to about 15%, by weight, organic water repellent binder.

14. The bait carrier of claim 1, wherein said bait carrier further comprises from about 4% to about 10%, by weight, anticaking agent.

15. The bait carrier of claim 1, wherein said bait carrier further comprises an antioxidant in a proportion not to exceed 0.5%, by weight, of said bait carrier.

16. A bait carrier for a pesticide including food waste comprising from about 40% to about 70%, by weight, carbohydrates; from about 5% to about 20%, by weight, protein; from about 10% to about 20%, by weight, fat; from about 5% to about 20%, by weight, water; from about 3% to about 8%, by weight, ash; and from about 2% to about 5%, by weight, fiber, said bait carrier having a size from about 10 mesh to about 40 mesh, U.S. Standard Sieve Series, and a density from about 30 pounds per cubic foot to about 40 pounds per cubic foot.

* * * * *